US008282274B2

(12) United States Patent  (10) Patent No.: US 8,282,274 B2
Pang et al.  (45) Date of Patent: Oct. 9, 2012

(54) REMOTE TEMPERATURE SENSING DEVICE

(75) Inventors: Yuk-Wa Pang, Hong Kong (HK); Ho Wai Phyllis Leung, Hong Kong (HK); Chun-Kong Joseph Chan, Hong Kong (HK); Kin Wah Kong, Markham (CA); Yat-Pui Wong, Hong Kong (HK); Kin-Ip Li, Hong Kong (HK)

(73) Assignee: Autovision Technology Limited, Kwai Chung (HK)

( * ) Notice: Subject to any disclaimer, the term of this patent is extended or adjusted under 35 U.S.C. 154(b) by 544 days.

(21) Appl. No.: 12/459,335

(22) Filed: Jun. 30, 2009

(65) Prior Publication Data

US 2010/0329301 A1  Dec. 30, 2010

(51) Int. Cl.
G01K 1/16 (2006.01)
G01J 5/00 (2006.01)
(52) U.S. Cl. ........................................ 374/121; 374/120
(58) Field of Classification Search .................. 374/121, 374/120
See application file for complete search history.

(56) References Cited

U.S. PATENT DOCUMENTS

| 2006/0007984 | A1* | 1/2006 | Bellifernine | 374/121 |
| 2006/0103742 | A1* | 5/2006 | Kubo et al. | 348/241 |
| 2007/0153871 | A1* | 7/2007 | Fraden | 374/121 |
| 2008/0154138 | A1* | 6/2008 | McQuilkin | 600/473 |
| 2009/0238238 | A1* | 9/2009 | Hollander et al. | 374/121 |
| 2009/0294667 | A1* | 12/2009 | Gorian et al. | 250/330 |
| 2009/0326383 | A1* | 12/2009 | Barnes et al. | 600/476 |
| 2012/0086450 | A1* | 4/2012 | Crowley et al. | 324/315 |

FOREIGN PATENT DOCUMENTS

GB  2441009 A  *  2/2008

\* cited by examiner

Primary Examiner — Lisa Caputo
Assistant Examiner — Jamel Williams
(74) Attorney, Agent, or Firm — Jason P. Mueller; Adams and Reese LLP

(57) ABSTRACT

A temperature sensing device for remotely detecting the temperature of a subject having an identifying feature and a target zone in a fixed relationship to the identifying feature comprising: a distance sensor which measures the distance between the subject and the distance sensor; a temperature sensor for measuring a temperature difference in a sensing zone; a digital image capture device for capturing a digital image of the subject; a means of tilting at least the temperature sensor along at least one axis, and preferably tilting and panning along two axes; a controller that actuates the tilting means; and a support for supporting the distance sensor, the temperature sensor and the digital image capture device; wherein the controller tilts the distance sensor using the tilting means to reduce the distance between the target zone and the sensing zone; and a temperature sensor that measures a temperature difference proximate to the target zone, to detect elevated temperature illness in humans or animals.

13 Claims, 4 Drawing Sheets

REMOTE TEMPERATURE SENSING DEVICE

FIELD OF THE INVENTION

A remote temperature sensing device for measuring the temperature of an individual or an animal at a distance.

BACKGROUND OF THE INVENTION

In airports, train stations and in other places of mass transportation for humans and for animals ('subjects'), it is known to screen individuals or animals for elevated temperature or other signs of illness. This is done to curtail the spread of illness caused by infectious disease.

In the past, such screening was done initially through subjective observation. A screening officer would simply observe a subject and look for signs of illness such as sweating, disorientation, flushed skin tone and coughing as indications that such a subject is ill and should be isolated from other subjects passing through the transportation hub.

More recently, there have been several technologies developed for screening subjects by measuring temperature, because elevated body temperature is a strong general indication of illness, including some contractual illnesses in both humans and animals. Such technologies have included thermometers, but thermometers have been problematic in a high-volume screening environment for two reasons. First, they are slow to react, which increases the time to measure temperature and thereby also increases operator error. Second, thermometers are difficult to sterilize because they come into direct contact with the subject. The increased chance of erroneous measurements and the problems with sterilization thereby greatly increase the chance of the spread of some contractual illnesses.

There are temperature sensors which measure temperature less invasively than a thermometer by using infrared radiation to measure temperatures at very short distances. Some infrared thermometers operate by being in contact with the skin of the subject. Other infrared thermometers operate at a distance of a few inches from the forehead of the subject, or from other sensing zones of the subject.

One of the principal challenges of using such methods is testing large numbers of individual subjects passing through a transportation hub or other building for symptoms of illness. The process can be slow if each individual has to be tested separately.

Some prior art temperature sensing devices scan individuals automatically using infrared sensing technology, and retrieve the results. The scanning process is typically done by passing infrared radiation over the subject's body or portion of their body to measure their temperature. There are three main difficulties with such devices. First, they must typically be manually re-adjusted to accommodate subjects of different heights.

Second, because the focal lengths of the infrared sensors are fixed, subjects must stand within a specific distance range from the device in order to provide an accurate reading. Because there is no facility to measure accurately the subject's distance in existing devices, the subject and operator usually do not know if a reading is erroneous.

Finally, because the infrared device must pass across the subject in a scanning motion, performing the scan and producing results could take between approximately tens of seconds to several minutes.

This time frame is typically too long to effectively test large numbers of subjects and prevent the spread of disease, while maintaining flow through such facilities. There is therefore a need for a remote temperature sensing device that automatically tests the subject, but also automatically measures distance, and that further adjusts to accommodate the height of the subjects approaching the temperature sensor.

SUMMARY OF THE INVENTION

The invention is directed to a temperature sensing device for remotely detecting the temperature of an subject having an identifying feature and a target zone in a fixed relationship to the identifying feature comprising:
- a distance sensor which measures the distance between the subject and the distance sensor;
- a temperature sensor for measuring a temperature in a sensing zone;
- a digital image capture device for capturing a digital image of the subject;
- a means of tilting at least the temperature sensor along at least one axis;
- a controller that actuates the tilting means; and
- a support for supporting the distance sensor, the temperature sensor and the digital image capture device;

wherein the controller tilts the distance sensor using the tilting means, by identifying the position of the identifying feature in the image, determining the location of the target zone based on the distance to the subject and the position of the identifying feature in the image, and then tilting the distance sensor to reduce the distance between the target zone and the sensing zone.

BRIEF DESCRIPTION OF THE DRAWINGS

Embodiments of the invention will be described by way of example and with reference to the drawings in which.

DETAILED DESCRIPTION OF THE INVENTION

Figure 1:
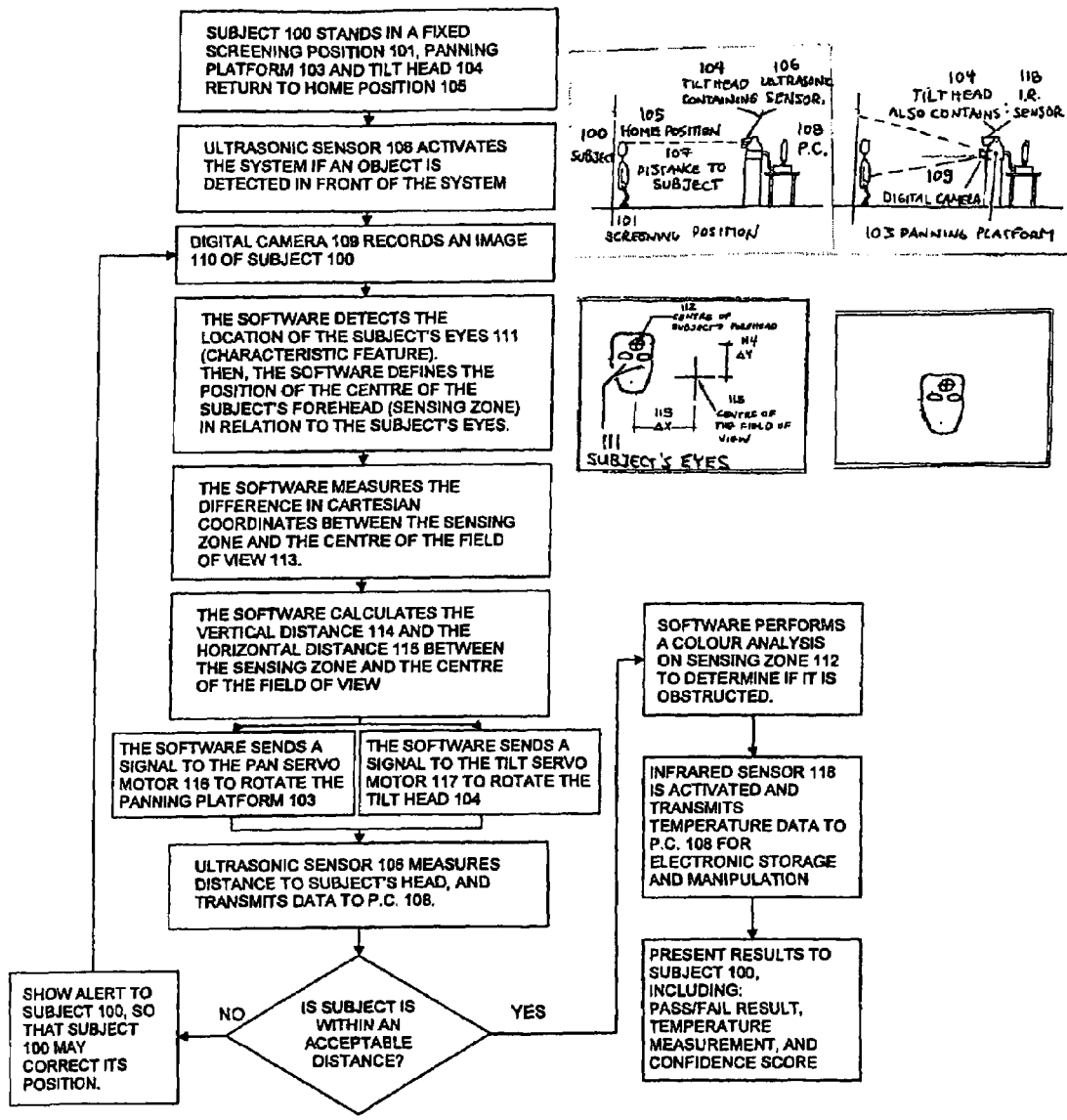
FIG. 1 is an illustrated functional block diagram which outlines the steps of the screening process.

FIG. 1 shows a flow chart of the process that may be followed by one embodiment of the present invention while in service. In this embodiment, a subject 100 stands in a fixed screening position 101. The panning platform 103 and tilt head 104 return to the home position 105, which is located approximately at the height of an average subject.

The invention includes a means of detecting the presence of a subject in front of the device. In this embodiment, the ultrasonic sensor 106 is active and transmits a signal to the PC 108 as soon as a subject steps in front of the device. Alternate sensing means may be used to detect the subject's presence, including other optical sensors, position sensors, or mechanical switches located at the screening position 101. In addition, the subject may be detected by being required to push a button, pull a trigger or step on a pedal.

The invention includes a means of capturing and storing a digital image. In this embodiment, a digital camera 109 captures a digital image 110 of the subject 100. The image data is stored and manipulated using a P.C. 108, as shown in this embodiment. The means used to capture and store a digital image are not limited to a digital camera. Other means, such as a video camera capable of storing a digital image, may be used.

The invention includes a means of recognizing an identifying feature 111 in a digital image. In this embodiment, the software detects the position of the subject's eyes (the identifying feature used in this embodiment). The scope of this invention is not limited to other identifying body features, such as the subject's nose, neck, chin or ears.

Further, the manipulation and storage of the image data is not limited to a P.C. 108 and its software. In an alternative embodiment, the image may be stored internally and manipulated using a controller in conjunction with firmware and an interactive human interface.

The invention includes a means of determining the vector distance between the target zone 112 and the centre of the field of view 113. In the present embodiment, the software calculates, in two dimensional Cartesian coordinates, the difference between the centre of the subject's forehead 112 (the target zone) and the centre of the field of view 113. In this embodiment, the software uses the known fixed distance to the screening position and the vertical 114 and the horizontal 115 distances between the centre of the subject's forehead 112 and the centre of the field of view 113 to calculate the pan angle and the tilt angle required to bring the centre of the field of view 113 into alignment with the centre of the subject's forehead 112.

The calculation of the vector distance is not limited to using two-dimensional Cartesian coordinates. Alternative means, such as polar coordinates or any other coordinate system may be used to calculate the vector distance between the target zone 112 and the centre of the field of view 113 ('vector distance').

The invention includes a means of rotating the remote temperature sensing means about at least one axis. In the present embodiment, the infrared sensor 106 rotates about a primary axis (tilt) and also rotates about a secondary axis (pan). In the present embodiment, the P.C. 108's software translates both the pan and tilt angles into codified electrical signals for a pan servo motor 116 and a tilt servo motor 117. The present embodiment uses an open loop control algorithm; that proceeds through only one control iteration of image-taking, calculating, and moving (tilting and panning) before sensing temperature.

Figure 2:
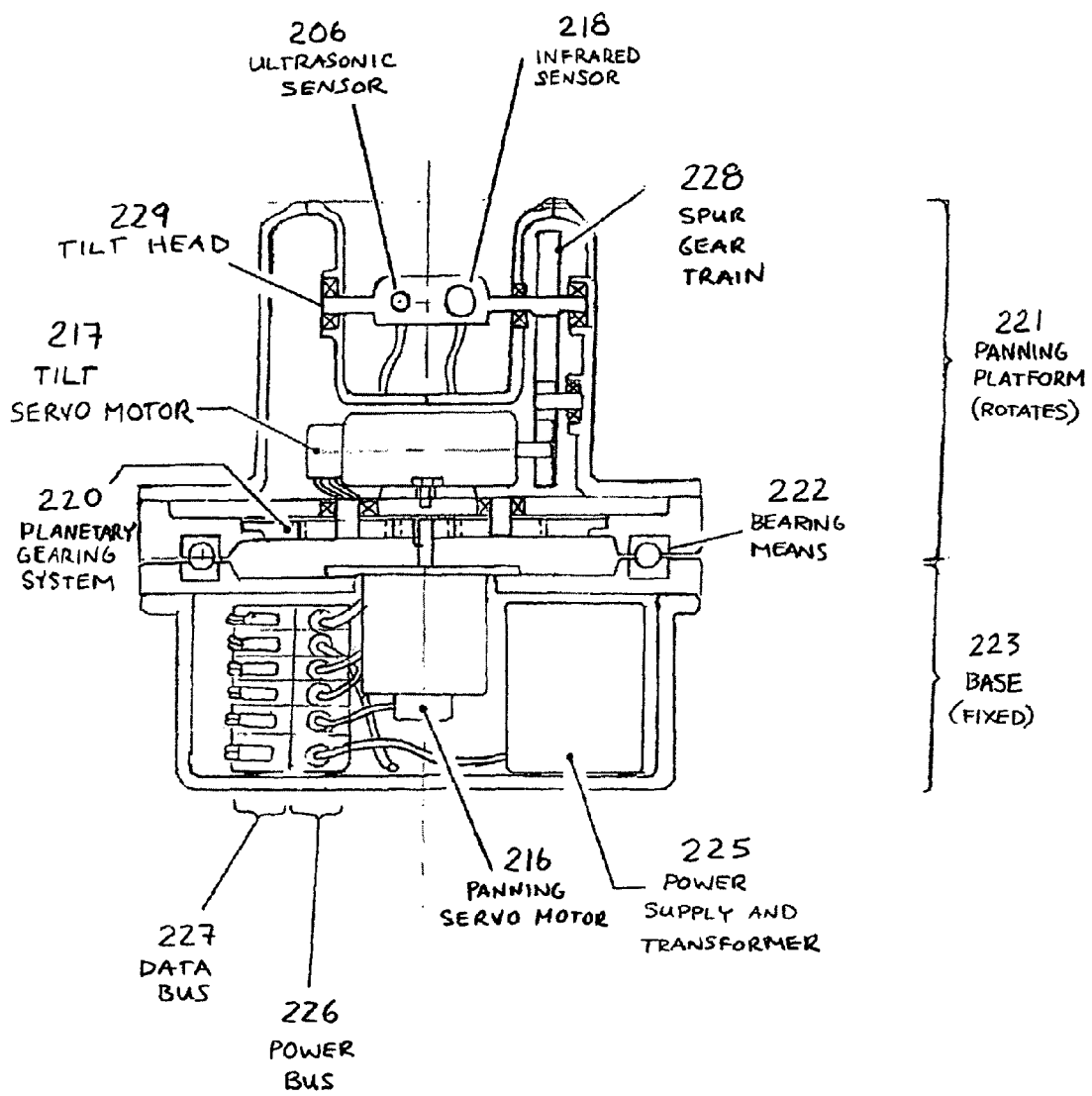
FIG. 2 is a sectional view through the centre of the device, cut parallel to the frontal plane along A-A in FIG. 4, in one embodiment of the current invention.
Figure 3:
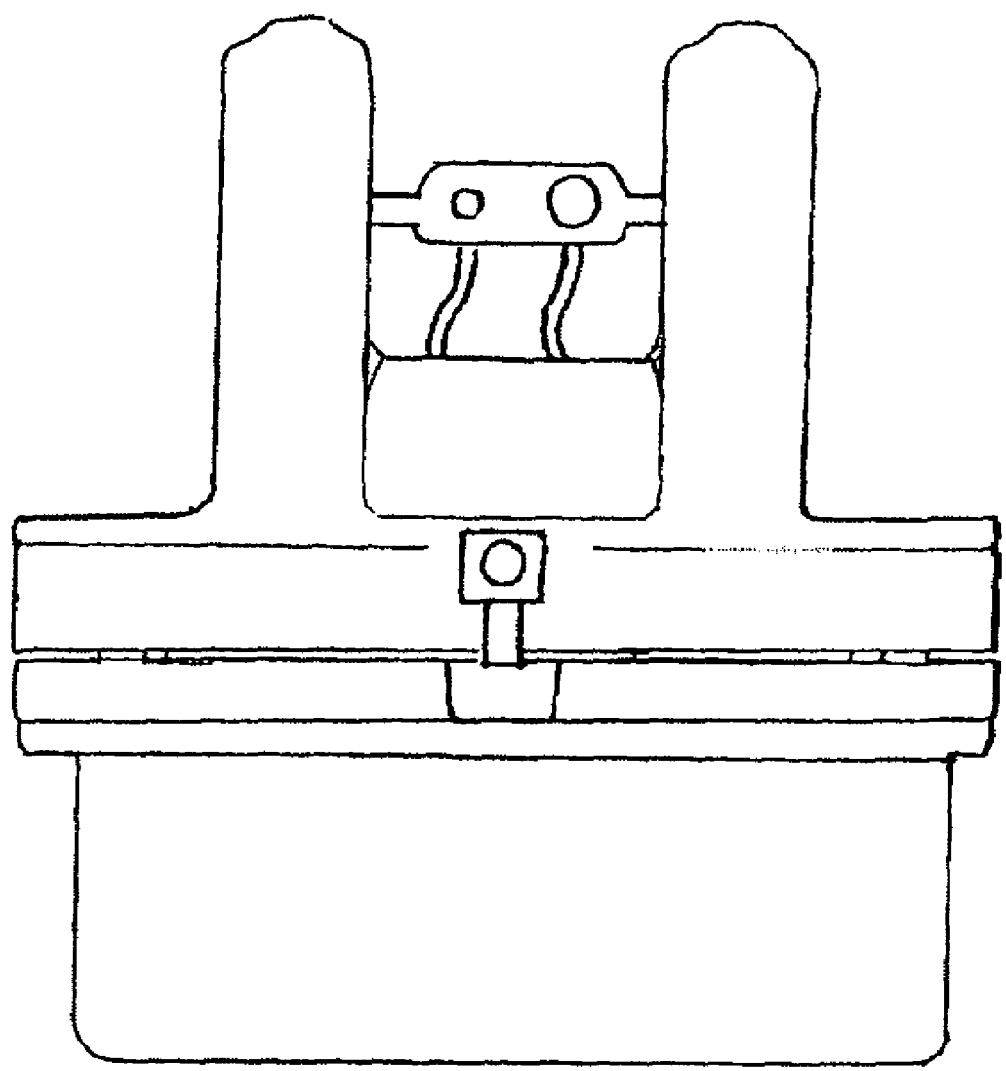
FIG. 3 is a frontal view of the device in one embodiment of the current invention.
Figure 4:
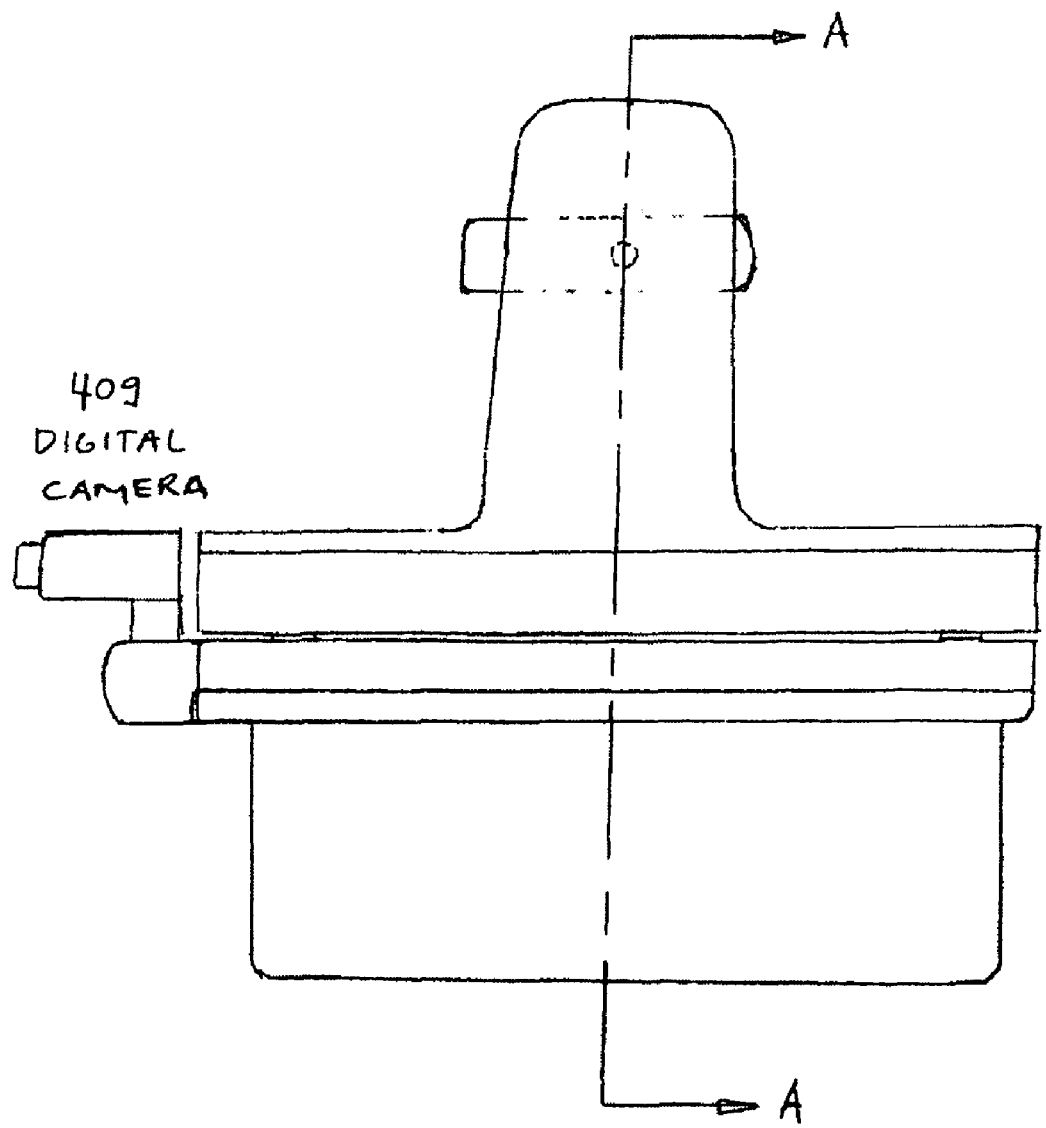
FIG. 4 is a side view of the device in one embodiment of the current invention.

In FIG. 2, the present embodiment of the invention uses a panning servo motor 216, in conjunction with a planetary gearing system 220 to rotate the panning platform 221 and all its attachments; along a bearing means 222, while the base 223 remains fixed.

To tilt the sensing means 106/206 and 1181218, the present embodiment uses a tilt servo motor 117/217, in conjunction with a spur gear train 228 and a tilt head 229. The tilt head 229 houses the ultrasonic sensor 206 and the infrared sensor 218 and is used to tilt both sensors together.

The present invention is not limited to tilting the sensing means by employing a spur gear train to transmit power to the sensing means. In alternative embodiments, the sensing means may be tilted using a chain and a sprocket arrangement, or using a gear and track arrangement.

Further, the sensing means 206 and 218 need not be necessarily fixed within a tilt head. In an alternative embodiment, the sensing means may be fixed to a mounting bracket attached to a shaft.

The invention includes a means to rotate the remote temperature sensing means about at least one axis. In the present embodiment, the device rotates the remote temperature sensing means 118/218 and the distance sensing means 106/206 about two axes, to pan and tilt the device in the direction of the target zone 112.

The invention includes a means of remotely measuring the distance to the subject. In the present embodiment, the ultrasonic sensor 106 is used to remotely measure the distance to the subject's head 107. The use of an ultrasonic sensor in this example does not preclude the use of other remote distance sensing means in this invention, such as a laser. This invention also does not preclude coordinating multiple sensing means, such as an optical transmitter and receiver to determine the presence of a subject in conjunction with the known, fixed horizontal distance of the screening position 101 to the ultrasonic sensor 106 to determine the distance to the subject's head 107.

In the present embodiment, the distance data is stored and manipulated using a P.C. 108. In an alternative embodiment, the distance data may be stored and manipulated internally on a controller.

The invention includes a means of detecting an obstruction in front of the sensing zone. In the present embodiment, the device tests for obstructions in a sensing zone 112, where the temperature data would be measured. The centre of the sensing zone 112 is defined, in this embodiment, by a fixed vector distance from the identifying feature 111. In the present embodiment, the P.C. 108's software is programmed to define the size of the sensing zone, and to determine the position of the target zone 112 from the identifying feature 111. The P.C. 108's software then accepts or rejects the image 110 after analyzing the image's colour profile and comparing it against a known threshold.

The two tasks of establishing the characteristics of the sensing zone and analyzing the colour profile of the image are not limited to the P.C. 108 and its software. In an alternative embodiment, characterizing the sensing zone 112 and analyzing its profile could be executed by an internal storage and manipulation means, such as a controller in conjunction with firmware and an interactive human interface. For example, the interface may consist of a display screen mounted on the reverse side of the device, which may feature on-screen touch buttons to allow the user to manipulate the image and execute commands. In an alternative embodiment, the display screen may also be used to communicate the results of a scan of an individual to an operator.

The invention requires a means of remotely measuring a difference in temperature within a sensing zone. In the present embodiment, this is achieved using an infrared sensor. The device may be used to calculate the actual temperature of the subject by calibrating the sensor using a known ambient temperature, based on a fixed focal length. The temperature of the target zone may also be calculated by measuring the temperature at the sensing zone using the temperature sensor and adjusting the temperature to accommodate for the distance between the device and the target. Other remote temperature sensing means may be employed which have similar limitations.

The invention requires a means of supplying electrical power to its components. In the present embodiment, electrical power is supplied using a power supply and a transformer 225 to the following components (collectively hereinafter referred to as 'the electrical components'), and distributes power to these using a power bus 226: servo motors 216 and 217, the remote distance sensing means 206, the remote temperature sensing means 218, and the digital camera 109/409 (not shown in FIG. 2).

The data connections between the electrical components and the P.C. 108 may be consolidated internally using a data bus 227, which would allow for a single, known cable interface between the P.C. 108 and the data bus 227 (e.g. eSATA 3,000, SATA 300, SATA 150, PATA 133, SAS 300, SAS 150, FireWire 3200, FireWire 800, FireWire 400, USB 3.0, USB 2.0, Ultra-320 SCSI, Fibre Channel over optic fiber, Fibre Channel over copper cable, InfiniBand), according to industry standards.

The invention is not limited to wired data connections between the devices and the P.C. 108. In the alternative, a wireless data connection could be used instead, according to industry standards.

A controller implemented in accordance with the present invention may comprise a computer system, microprocessor or other digital circuitry having memory and a processor to execute software, or may comprise any analog or digital circuitry that directly operates the device without software. The controller may also comprise a master-slave or server and client structure, where processing occurs remotely from the device, or the device is directed from a remote location automatically.

The software may include executable code stored in a memory for execution by a processor. A memory may include any static, transient or dynamic memory or storage medium, including without limitation read-only memory (ROM) or programmable ROM, random access registers memory (RAM), transient storage in registers or electrical, magnetic, optical or electronic storage media. The software does not include a signal in transmission, or a carrier wave. A processor includes any device or set of devices, howsoever embodied, whether distributed or operating in a single location that is designed to or has the effect of carrying out a set of instructions, but excludes an individual or person.

The foregoing description illustrates only certain preferred embodiments of the invention. The invention is not limited to the foregoing examples. That is, persons skilled in the art will appreciate and understand that modifications and variations are, or will be, possible to utilize and carry out the teachings of the invention described herein. Accordingly, all suitable modifications, variations and equivalents are intended to fall within the scope of the claims.

The invention claimed is:

1. A temperature sensing device for remotely detecting the temperature of a subject having an identifying feature and a target zone in a fixed relationship to the identifying feature comprising:
    a means of detecting the presence of the subject in a screening position;
    a distance sensor which measures the distance between the subject and the distance sensor;
    a temperature sensor for measuring a temperature in a sensing zone on the subject;
    a digital image capture device for capturing a digital image of the subject;
    a means of tilting at least the temperature sensor along at least one axis;
    a controller that actuates the tilting means; and
    a support for supporting the distance sensor, the temperature sensor and the digital image capture device;
    wherein the controller tilts the temperature sensor using the tilting means, by identifying the position of the identifying feature in the image, determining the location of the target zone on the subject based on the distance to the subject and the position of the identifying feature in the image, and then tilting the distance sensor to reduce the distance between the target zone and the sensing zone.

2. The device of claim 1, wherein the tilting means also tilts the distance sensor.

3. The device of claim 1, wherein the tilting means also tilts the digital image capture device.

4. The device of claim 1, wherein the distance sensor comprises an ultrasonic sensor.

5. The device of claim 1, wherein the temperature sensor comprises an infrared sensor.

6. The device of claim 5, wherein the infrared sensor is calibrated to detect a difference in temperature from the expected temperature of the target zone.

7. The device of claim 1, wherein the digital image capture device comprises a video camera with the ability to capture a digital image.

8. The device of claim 1, wherein the controller is incorporated into a housing that is proximate to the digital image capture device.

9. The device of claim 1, wherein the controller comprises a computer in communication with the tilting means through a communication means.

10. The device of claim 1, further comprising a display device for displaying the results of a scan of an individual to an operator.

11. The device of claim 1, wherein the tilting means comprises a servo motor.

12. The device in claim 1, wherein measuring a temperature in a sensing zone comprises measuring the temperature using the temperature sensor and adjusting the temperature to accommodate for the distance between the device and the target.

13. A method of scanning a human or an animal for elevated temperature using a temperature sensing device, comprising:
    providing a temperature sensing device having a distance sensor, a temperature sensor, a means of capturing a digital image and an electronic controller having storage and a tilting means for tilting the distance sensor and the temperature sensor together; and
    capturing a digital image of a target;
    recognizing an identifying feature in the digital image and defining the position of a target zone on the target relative to the distance of the identifying feature;
    determining the distance between the target zone and a sensing zone on the target;
    tilting at least the temperature sensor to reduce the distance between the target zone and the sensing zone; and
    calculating the temperature of the target zone by measuring the temperature at the sensing zone using the temperature sensor and adjusting the temperature to accommodate for the distance between the device and the target.

* * * * *